United States Patent
List

(10) Patent No.: US 8,057,156 B2
(45) Date of Patent: Nov. 15, 2011

(54) TRANSFER UNIT FOR TEST ELEMENTS

(75) Inventor: Hans List, Hesseneck-Kailbach (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 536 days.

(21) Appl. No.: 12/183,731

(22) Filed: Jul. 31, 2008

(65) Prior Publication Data

US 2009/0035120 A1    Feb. 5, 2009

(30) Foreign Application Priority Data

Aug. 2, 2007  (EP) .................................... 07113687

(51) Int. Cl.
*B65H 1/00*   (2006.01)
*B65G 1/00*   (2006.01)
*B65G 57/00*  (2006.01)
*G01N 21/75*  (2006.01)
*G01N 21/00*  (2006.01)

(52) U.S. Cl. ... 414/806; 414/802; 414/808; 414/222.01; 414/222.12; 414/287; 422/400; 422/63; 422/64; 422/65

(58) Field of Classification Search .................. None
See application file for complete search history.

(56) References Cited

U.S. PATENT DOCUMENTS

| | | | |
|---|---|---|---|
| 6,159,424 A | 12/2000 | Kauhaniemi et al. | |
| 6,203,760 B1 * | 3/2001 | van der Plaats et al. | 422/63 |
| 6,534,017 B1 | 3/2003 | Bottwein et al. | |
| 6,827,899 B2 | 12/2004 | Maisey et al. | |
| 2002/0057993 A1 | 5/2002 | Maisey et al. | |
| 2005/0106048 A1 * | 5/2005 | Chisholm et al. | 417/437 |
| 2007/0173739 A1 * | 7/2007 | Chan | 600/583 |
| 2009/0186420 A1 * | 7/2009 | Kahlman et al. | 436/150 |

FOREIGN PATENT DOCUMENTS

| | | |
|---|---|---|
| EP | 1 203 563 | 5/2002 |
| EP | 1 362 551 | 11/2003 |
| EP | 1 301 784 | 10/2005 |

* cited by examiner

*Primary Examiner* — Brian J Sines
*Assistant Examiner* — Jennifer Wecker
(74) *Attorney, Agent, or Firm* — Bose McKinney & Evans LLP

(57) ABSTRACT

The invention relates to an analysis apparatus with an analysis device for analyzing body fluids, and a magazine for test elements with a fresh supply container and a transfer unit that comprises a transfer element. At least one aperture for receiving a test element is formed in the circumferential surface of the transfer element. A waste container is provided in which used test elements are stored again after use.

23 Claims, 2 Drawing Sheets

TRANSFER UNIT FOR TEST ELEMENTS

This application claims priority to EP 07113687.3, filed Aug. 2, 2007, which is hereby incorporated by reference in its entirety.

BACKGROUND

The present invention relates to a transfer unit for test elements that are used for detection of an analyte in a body fluid.

Many different kinds of systems and devices for analysis of body fluids are known, in particular, systems in which a large number of test elements are stored. The test elements are generally strip-shaped and are accommodated in a magazine. Disk-shaped storage systems or drum-shaped storage systems are suitable for storing test elements. However, disk-shaped or drum-shaped magazines are only practicable for a small number of 5 to 20 test elements. For test elements up to this number, disk-shaped and drum-shaped magazines are good ways of ensuring space-saving storage of test elements.

If larger quantities of test elements are to be stored, however, a disk magazine or drum magazine becomes unmanageable since, in order to receive a larger number of test elements, the diameter of the disk or drum magazine must be increased. For test elements numbering 20 or more, stack magazines according to U.S. Pat. No. 6,827,899 can be used. The stack magazine known from U.S. Pat. No. 6,827,899 stores fresh test elements, but requires that the user dispose of individual used test elements contaminated with a body fluid.

U.S. Pat. No. 6,159,424 relates to a device for handling measurement strips which are used to collect fluid samples, for example, blood samples. The measurement strips have a porous material for absorbing the fluid sample and for analysis thereof. The measurement device according to U.S. Pat. No. 6,159,424 has a reservoir which is designed as a composite structure for measurement strips that take up samples, it has another reservoir for receiving used measurement strips, and also has a delivery mechanism for measurement strips. The device known from U.S. Pat. No. 6,159,424, with the reservoir for unused measurement strips and the reservoir for used measurement strips, is preferably integrated inside a housing part.

U.S. Pat. No. 6,534,017 relates to a storage device for test elements. The test elements are held inside a magazine, and the test elements have one or more test zones which are arranged lying next to one another on a rectangular support. The magazine comprises at least one pair of guide grooves which are arranged lying opposite each other and into which the test elements are inserted in such a way that they lie directly next to one another and the edges of contiguous supports abut one another. According to a further aspect of U.S. Pat. No. 6,534,017, a slide is proposed which is used in addition to the magazine and which serves to move a layer of test elements along the guide grooves to the opposite end and to dispense test elements from the magazine.

One disadvantage of the devices discussed above is that the person using an analysis system or an analysis device for examining a human body fluid for an analyte has to dispose of contaminated test elements himself, which is regarded as highly unsatisfactory and needs to be remedied.

SUMMARY OF THE INVENTION

The present invention provides a transfer device with which a test element, for example, of strip-shaped configuration, is removed from a fresh supply container, delivered to a work position, and then conveyed into a waste container for contaminated test elements. In exemplary embodiments, the transfer device can be operated without using an electrical or pneumatic drive or the like. The transfer device can be a simple structure that can be operated by simple actuation of a rotary button or lever in one direction and then another. For a fully automatic system in which the user does not have to perform this work, any actuator can be used that is capable of executing these short pivoting movements.

To drive the transfer unit according to exemplary embodiments for conveying test elements into a work position and out of a work position into a waste container, it is possible to use the voltage source that is already present on an analysis device for analyzing body fluids. To trigger a pivoting movement of a transfer element of the transfer unit, it is possible to use shape-memory wires that can be connected to the voltage source of the analysis device or of the analysis system. In one embodiment, two substantially parallel shape-memory wires can be used which, when a current is passed through them, are heated to above their transformation temperature and, accordingly, contract against considerable forces. When the voltage is switched off, they cool again and in so doing change their modulus of elasticity, as a result of which they can be extended with low forces.

The transfer unit in certain embodiments comprises a substantially semicylindrical transfer element. The transfer element is movable about a pivot axle. A fresh supply container of test elements is placed against the circumferential surface of the transfer element. The fresh supply container of test elements can, for example, comprise a number of test elements arranged in a stack formation one above the other. They are accommodated in a sleeve-shaped container and are acted upon by a spring element. The end face of the sleeve-shaped container in which the unused test elements are held is provided with an elastomeric seal which is placed against the circumferential surface of the transfer element of the transfer unit. This reduces contamination by air humidity of the fresh supply of unused test elements. The action of the spring on the fresh supply of stacked and unused test elements ensures that a fresh, unused test element is always available for use at the circumferential surface of the transfer element of the transfer unit.

At an angle with respect to the fresh supply container, a waste container is assigned to the circumferential surface of the transfer element of the transfer unit. At its top end, the waste container comprises a stripper with which, when the transfer element is pivoted about the pivot axle, a contaminated test element arranged in a work position on the circumferential surface of the transfer element and to be removed therefrom is conveyed from the circumferential surface of the transfer element and into the waste container.

The contaminated test elements are also stored in the waste container again in a stack formation, since the contaminated test elements successively stripped off after use from the circumferential surface of the transfer element are conveyed in a stack formation into the waste container in which a further spring element is arranged. Along a section of the circumference, the transfer element comprises a recess inside which the stripper moves, the stripper removing the contaminated test elements from their work position and delivering them to the waste container.

The fresh supply container in which the unused test elements are stored in a stack formation, is acted upon on the one hand by a spring element and at all times placed against the circumferential surface of the transfer element, and on the other hand is acted upon by an elbowed lever which interacts with an abutment. A first shape-memory wire and a second shape-memory wire are secured on the elbowed lever such that they engage with approximately the same radius to the lever fulcrum. The respective other ends of the shape-memory wires, which extend substantially parallel to each other, are secured to the left and right of the pivot point of a carrier which moves the transfer element of the test strip magazine. If one of the wires is heated, it contracts and in so doing pivots the carrier, while the unheated wire is expanded and in so doing moves the transfer element such that the receiving groove for the test strip to be worked on is placed in front of the fresh supply container or waste container. If both wires are unheated, a torsion spring with moment jump acts on the carrier such that the transfer element remains in the work position.

The test elements stored in the fresh supply container are preferably strip-shaped test elements. It is not important whether a lancet or a sampler is integrated in these strip-shaped test elements. The transfer unit according to this embodiment used for conveying test elements comprises the fresh supply container, the waste container and the transfer unit. These structural parts can all be component parts of an analysis device or component parts of a magazine storing test elements, or they can be distributed between the magazine and the analysis device. Any desired combinations in the distribution of the components are possible.

The component parts of the system of movement can be arranged fixedly on the device, such that the disposable test strip magazine only comprises the fresh supply container with sleeve and seal, the transfer element and the waste container.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
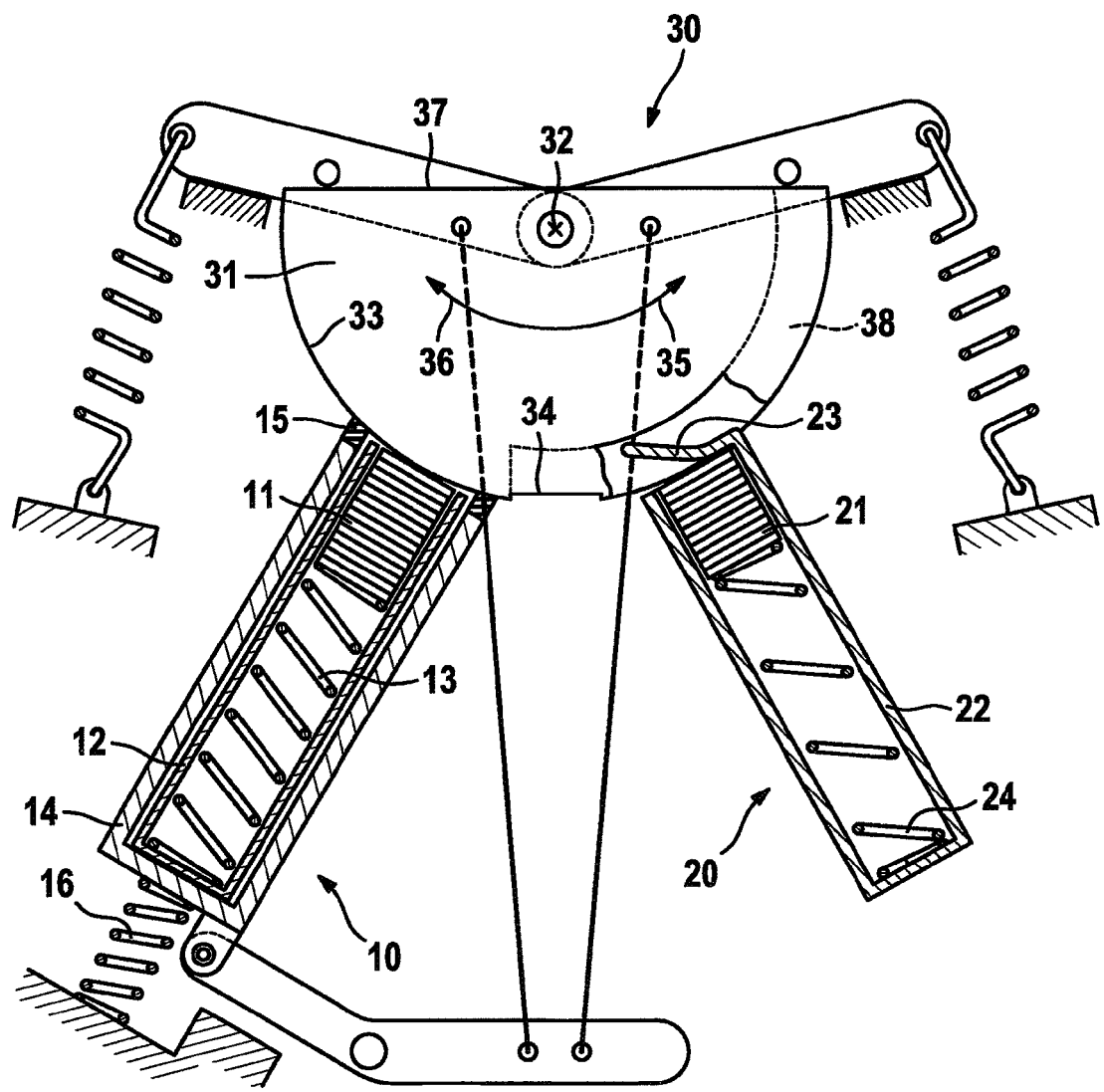
FIG. 1 is a schematic representation of a transfer unit in accordance with one embodiment of the present invention showing a fresh supply container, waste container and transfer element.

The main components of the transfer unit used for test elements can be seen in FIG. 1, namely, a fresh supply container, a transfer element and a waste container.

FIG. 1 shows that a fresh supply container 10 comprises a sleeve 14. Inside the sleeve 14 there is a frame 12 or a can-shaped container in which test elements 11 are stored in a stack formation. The test elements 11, which bear on one another with their lengthwise surfaces, are acted upon by a first spring element 13, which is supported on the bottom of the frame or can 12, and are placed against a circumferential surface 33 of a transfer element 31. The frame or can is enclosed by a sleeve 14 at whose open end, directed toward the rounded or circumferential surface 33 of the transfer element 31, there is attached an elastomeric seal 15. A second spring element 16, which is supported on a support surface, acts on the sleeve 14 such that the elastomeric seal 15 is pressed continuously against the circumferential surface 33 of the transfer element 31, as a result of which the strip-shaped test elements 11 are protected from harmful external influences, e.g., moisture.

A waste container 20 is located at an angle with respect to the circumferential surface 33 of the transfer element 31. Used test elements 21 are received in the waste container 20. The used test elements 21 are stored inside the waste container 20 once again in a stack formation. The supply of used test elements 21 in the waste container 20 is also acted upon by a third spring element 24, by which the stack formation in the waste container 20 is maintained. At the top end of the waste container 20 there is at least one stripper element 23, which engages into a recess 38 formed on the circumference 33 of the transfer element 31. The transfer element 31 is mounted rotatably on a pivot axle 32. When the transfer element 31 swivels about the pivot axle 32 in a first direction of rotation 35, a worked, i.e., used test strip 21, previously placed in an aperture 34, is removed from the aperture 34 by the stripper element 23 and is conveyed into the waste container 20.

The transfer element 31 can be pivoted both in the direction of rotation 35 already mentioned and also in the clockwise direction 36, i.e., in a second direction of rotation 36. The transfer element is held in a center or "work" position by means of a torsion spring with "moment jump." This torsion spring, which in the zero point jumps from a leftward rotating moment to a rightward rotating moment, can be constructed in various ways. For the sake of clarity, here the following arrangement is chosen by way of example and is non-limiting.

Figure 2:
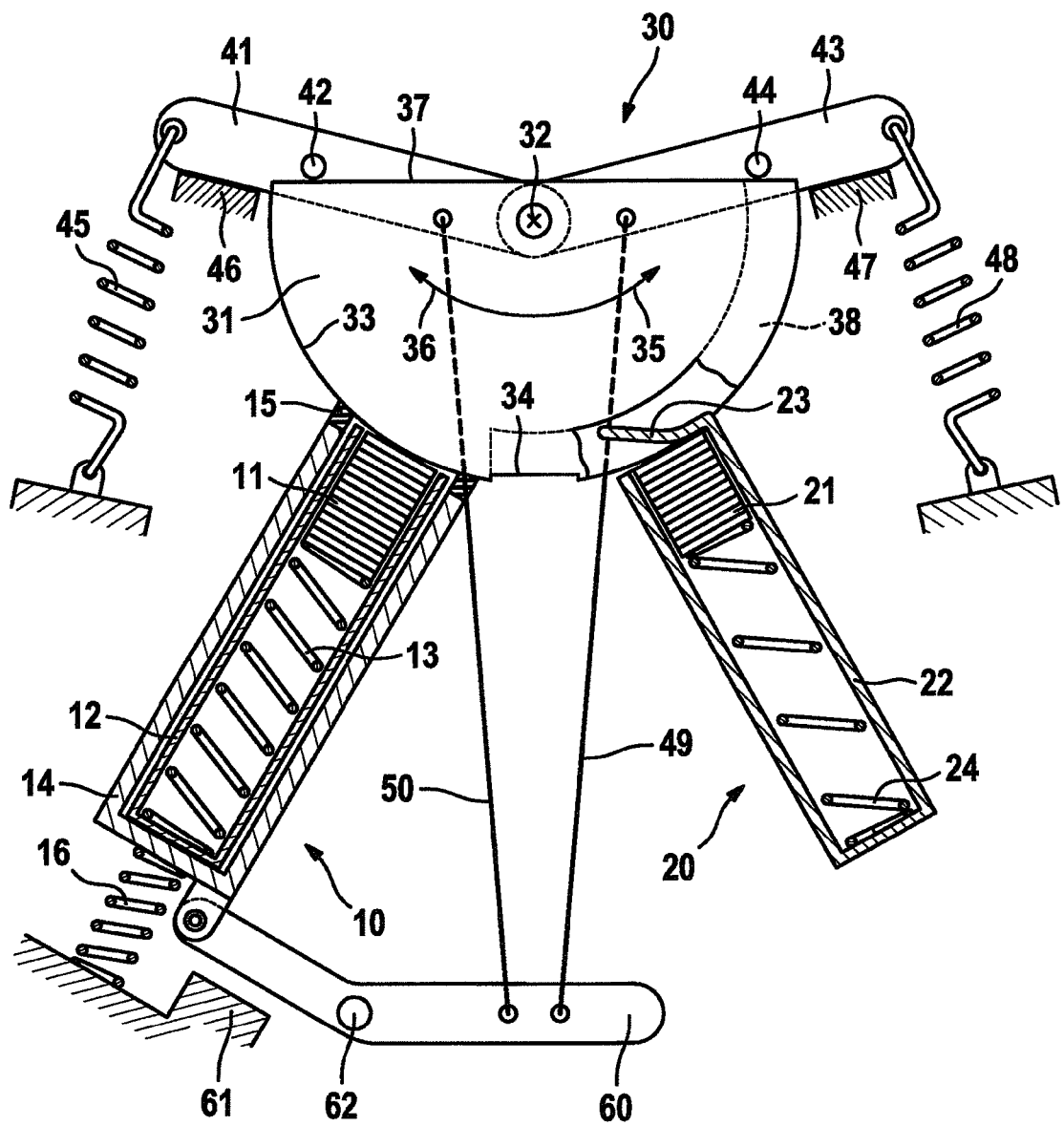
FIG. 2 is a schematic representation of the transfer unit of FIG. 1, shown with spring elements acting on the fresh supply container, waste container and transfer element assemblies, and with shape-memory wires connected to an elbowed actuating lever.

FIG. 2 shows spring elements that act on or actuate the individual components of the transfer unit, namely a fresh supply container, a transfer element and a waste container. It will be seen from the view according to FIG. 2 that two levers 41, 43 are mounted on the pivot axle 32 about which the semicircular transfer element 31 can pivot. The two levers 41 and 43 are drawn against abutments 46 and 47 by springs 45 and 48. They have carriers 42 and 44 that bear on the edge 37 of the transfer element 31. If the transfer element is now turned from its work position, e.g., in a counter-clockwise direction, the lever 43 is lifted from its abutment 47 and the spring force is supported on the edge 37 of the transfer element via the carrier 44, such that a torque of defined magnitude immediately acts against the rotation movement. Upon rotation in the clockwise direction, the levers, springs and abutments arranged in mirror symmetry have the same effect in the opposite direction. This ensures that the transfer element always returns to the work position against friction and residual forces in the actuator wires 49 and 50.

Underneath the fresh supply container 10 there is another lever 60, which is pivotable about another pivot axle 62. This lever 60 interacts with an abutment 61 and is in engagement with the lower end of the sleeve 14 of the fresh supply container 10, which is additionally acted upon constantly by the second spring element 16, pressing it against the circumferential surface 33 of the transfer element 31.

A first shape-memory wire 49 and a second shape-memory wire 50 are secured on the lever 60. Instead of straight wires, it is also possible, for example, to use coiled springs made of shape-memory alloy. These springs can analogously work by pressure instead of traction. For this, the fulcrum of the lever 60 has to be shifted in such a way as to ensure the opening function of the fresh supply container. The first and second shape-memory wires 49, 50 engage substantially with the same radius on the lever 60. The other ends of the shape-memory wires 49, 50 are secured to both sides of the pivot axle 32 on the transfer element 31 or on a carrier that moves.

For the transfer element 31 to be turned to a receive position such that an unused test element 11 can be removed from the fresh supply container 10 and transferred to aperture 34, current is passed through the first shape-memory wire 49, whereupon it contracts. This contraction of the first shape-memory wire 49 initially leads to an excursion of the lever 60 counter to the action of the spring element 16. In this way, the sleeve 14 of the fresh supply container 10 is pulled away from the circumferential surface 33 of the transfer element 31, and the contact between the elastomeric seal 15 and the circumferential surface 33 of the transfer element 31 is lost. At the end of this short excursion, the lever 60 sits on the abutment 61 such that further contraction of the first shape-memory wire 49 moves the transfer element 31 in the clockwise direction 36. When, in the course of this excursion, the aperture 34 formed in the circumferential surface 33 comes into position above the fresh supply container 10 (receive position), the first spring element 13 presses an unused test element 11 into the aperture 34.

When the flow of current through the first shape-memory wire 49 is then terminated, it cools down and becomes extensible again as soon as its temperature has dropped below the transformation temperature. By way of the lever 41 and the carrier 42 which is secured thereon and which acts on the edge 37 of the transfer element 31 moved in the second direction of rotation 36, the spring element 45 returns the transfer element 31 counter clockwise 35 back to its rest or work position shown in FIG. 2. In this work position, the unused test element 11 received in the aperture 34 can be used. In parallel with this, the first shape-memory wire 49 is relaxed to such a degree that the second spring element 16 presses the sleeve 14 of the fresh supply container 10 against the circumferential surface 33 of the transfer element 31 again, and the elastomeric seal 15 arranged at the open end of the sleeve 14 closes off and seals the supply of unused test elements 11.

After it is used, the test element held in aperture 34 is thus contaminated with body fluid and thus becomes a used test element 21 that is to be removed from aperture 34. Current is passed through the second shape-memory wire 50, and by means of the contraction of the second shape-memory wire 50, the lever 60 is moved about the pivot axle 62 again, and the elastomeric seal 15 is drawn counter to the action of the spring element 16, away from the circumferential surface 33 of the semicircular transfer element 31. The further contraction of the second shape-memory wire 50 causes the transfer element 31 to turn counter clockwise 35 into a dispense position, such that the used test strip 21 received in the aperture 34 on the circumference of the transfer element 31 moves in the direction of the at least one stripper element 23. The stripper element 23 located at the opening of the waste container 20 moves in a recess 38 provided for it in the circumferential surface 33 of the transfer element 31 and conveys the test strip, held in the aperture 34 of the transfer element 31, into the waste container 20. Inside the waste container 20, the used test elements 21 are collected in a stack formation, and they are held in this stack formation by the third spring element 24 arranged inside the waste container 20.

When the flow of current through the second shape-memory wire 50 is interrupted, it cools, drops below its transformation temperature and becomes extensible again. By way of the spring element 48 connected to the lever end of the lever 43, and the carrier 44 which is secured on the lever 43 and which acts on the edge 37 of the transfer element 31, the latter is moved back to its rest position shown in FIG. 2. Upon further relaxation of the second shape-memory wire 50, the second spring element 16 places the sleeve 14 of the fresh supply container 10 (and the frame 12 or can 12 received therein) back against the circumferential surface 33 of the semicircular transfer element 31 such that the elastomeric seal 15 closes off the supply of unused test elements 11 in stack formation inside the fresh supply container 10.

This arrangement ensures that the seal 15 is always lifted from the circumferential surface 33 of the transfer element 31 before the transfer element 31 moves from its rest position. Likewise, the transfer element always reaches the rest position again before the seal 15 touches the circumferential surface 33. In this way, both the force requirement and also the degree of wear of the seal are minimized. For this purpose, of course, the characteristic data of the actuators and the spring forces have to be adapted to one another, as is standard practice for a person skilled in the art in the field of device technology.

As the drive means for the required movements, it is also possible to use a combined cam mechanism, lifting magnets or similar suitable means. However, since each movement always entails only a brief switching operation, a pair of simple shape-memory actuators can typically be employed.

In an alternative to the design of the fresh supply container 10 shown in FIG. 2, sleeve 14 can be omitted. In this case, the frame 12 or receiving structure for the unused test elements is open, such that the entire system has to be sealed off or, alternatively, it is necessary to use test elements that are not sensitive to environmental influences. In this case, the actuators for the transfer of test strips can also be structures that directly generate torque, e.g. helical springs, torsion springs or the like.

In an alternative to the possible design of the transfer unit 30 shown in FIGS. 1 and 2, which includes the transfer element 31, the fresh supply container 10 and the waste container 20, the illustrated drives and their associated lever mechanisms 41, 43, 60 can be fixed component parts of the analysis device. By contrast, the fresh supply container 10, the waste container 20 and the transfer element 31 can be component parts of a magazine removable from the analysis device, or they can be distributed between analysis device and magazine.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A transfer unit for use with an analysis apparatus, comprising:
   a supply container configured to store and release unused test elements;
   a waste container configured to receive and store used test elements; and
   a transfer element having a rounded surface defining an aperture configured to hold a test element, the transfer element having a work position in which the aperture is positioned between the supply container and the waste container, the transfer element being movable from the work position in a first direction to a receive position in which the aperture is aligned with the supply container, the transfer element being movable from the work position in a second direction to a dispense position in which the aperture is aligned with the waste container;

wherein the supply container, the waste container and the transfer element are component parts of a magazine removable from the analysis device.

2. The transfer unit of claim 1, wherein the transfer unit is a component of an analysis apparatus.

3. The transfer unit of claim 1, wherein the supply container comprises a movable sleeve configured to enclose test elements in a stack formation.

4. The transfer unit of claim 1, wherein the waste container at an open end thereof comprises a stripper element configured for removing a used test element from the work position.

5. The transfer unit of claim 4, wherein the stripper element extends into a recess formed on the rounded surface of the transfer element.

6. The transfer unit of claim 1, wherein the transfer element is pivotable about a pivot axle and is held in the work position by a spring.

7. The transfer unit of claim 6, wherein the spring comprises a torsion spring which provides a first torque against the movement of the transfer element in the first direction and a second torque against the movement of the transfer element in the second direction.

8. The transfer unit of claim 1, further comprising shape-memory actuators which drive the transfer element.

9. The transfer unit of claim 1, wherein the actuators open the supply container.

10. The transfer unit of claim 1, wherein the transfer element is automatically moved from the work position after a seal of the supply container has been removed from the rounded surface.

11. The transfer unit of claim 10, wherein the seal again contacts the rounded surface when the transfer element returns to the work position.

12. The transfer unit of claim 1, wherein the transfer element is moved about a pivot axle by at least one of an electric motor, magnet, lever mechanism, or cam mechanism.

13. A transfer unit for use with an analysis apparatus, comprising:

a supply container configured to store and release unused test elements;

a waste container configured to receive and store used test elements;

a rotatable transfer element having a rounded surface defining at least one aperture that is configured to receive a test element;

the transfer element having a work position in which the aperture is located between an opening of the supply container and an opening of the waste container, the transfer element being rotatable from the work position in a first direction against a first torque to a receiving position in which the aperture is aligned with an opening of the supply container, the transfer element being rotatable from the work position in a second direction against a second torque to a waste position in which the aperture is aligned with an opening of the waste container; and a torsion spring which holds the transfer unit in the work position.

14. The transfer unit of claim 13, further comprising a first actuator wire connected to the transfer element and operable to rotate the transfer element from the work position to the position in which the aperture is aligned with the opening of the supply container.

15. The transfer unit of claim 14, further comprising a second actuator wire connected to the transfer element and operable to rotate the transfer element from the work position to the position in which the aperture is aligned with the opening of the waste container.

16. The transfer unit of claim 15, wherein the first and second actuator wires comprise shape-memory wires.

17. The transfer unit of claim 13, wherein the torsion spring supplies the first torque and the second torque.

18. The transfer unit of claim 13, wherein the supply container comprises a seal and a supply container spring which removably biases the seal against the rounded surface of the transfer unit.

19. The transfer unit of claim 18, further comprising a first lever connected to the supply container, actuation of the first lever moving the seal of the supply container away from the rounded surface of the transfer unit against the force of the supply container spring.

20. The transfer unit of claim 19, wherein the actuation of the first lever rotates the transfer element from the work position to the position in which the aperture is aligned with the opening of the supply container.

21. The transfer unit of claim 20, further comprising a first actuation wire connecting the first lever to the transfer element.

22. The transfer unit of claim 21, further comprising a second lever connected to the waste container, actuation of the second lever rotating the transfer element from the work position to the position in which the aperture is aligned with the opening of the waste container.

23. The transfer unit of claim 22, further comprising a second actuation wire connecting the second lever to the transfer element.

* * * * *